United States Patent
Wu et al.

(10) Patent No.: US 12,109,013 B2
(45) Date of Patent: Oct. 8, 2024

(54) ON-SKIN SENSING SYSTEM FOR DETECTING BLOOD FLOW STATUS IN POSTOPERATIVE FLAP AND RECONSTRUCTED LIMB

(71) Applicant: HUAZHONG UNIVERSITY OF SCIENCE AND TECHNOLOGY, Hubei (CN)

(72) Inventors: Hao Wu, Hubei (CN); Ganguang Yang, Hubei (CN); Jinwen Zhang, Hubei (CN)

(73) Assignee: HUAZHONG UNIVERSITY OF SCIENCE AND TECHNOLOGY, Wuhan (CN)

( * ) Notice: Subject to any disclaimer, the term of this patent is extended or adjusted under 35 U.S.C. 154(b) by 0 days.

(21) Appl. No.: 18/290,695

(22) PCT Filed: Sep. 28, 2021

(86) PCT No.: PCT/CN2021/121144
§ 371 (c)(1),
(2) Date: Jan. 19, 2024

(87) PCT Pub. No.: WO2023/039946
PCT Pub. Date: Mar. 23, 2023

(65) Prior Publication Data
US 2024/0260845 A1 Aug. 8, 2024

(30) Foreign Application Priority Data
Sep. 14, 2021 (CN) .......................... 202111074743.X (51) Int. Cl.
*A61B 5/0295* (2006.01)
*A61B 5/00* (2006.01)
(Continued)

(52) U.S. Cl.
CPC ............ *A61B 5/0295* (2013.01); *A61B 5/002* (2013.01); *A61B 5/02055* (2013.01);
(Continued)

(58) Field of Classification Search
CPC ... A61B 5/0295; A61B 5/002; A61B 5/02055; A61B 5/6832; A61B 5/725;
(Continued)

(56) References Cited

U.S. PATENT DOCUMENTS

| 2007/0032719 A1 | 2/2007 | Menon et al. |
| 2010/0059722 A1 | 3/2010 | Copp-Howland et al. |
| 2020/0163844 A1 | 5/2020 | Pang et al. |

FOREIGN PATENT DOCUMENTS

| CN | 101035860 A | 9/2007 |
| CN | 101137718 A | 3/2008 |

(Continued)

OTHER PUBLICATIONS

International Search Report and Written Opinion issued in PCT/CN2021/121144, dated May 25, 2022, 11 pages provided, with English translation of International Search Report.

(Continued)

*Primary Examiner* — Jonathan T Kuo
(74) *Attorney, Agent, or Firm* — HSML P. C.

(57) ABSTRACT

The present invention relates to the field of medical health monitoring. Disclosed in the present invention is an on-skin sensing system for detecting blood flow status in a postoperative flap and reconstructed limb, the system including a front-end status detection module and a back-end signal processing and outputting module. The front-end status detection module acquires, in real time, blood oxygen saturation and temperature statuses of postoperative flaps and reconstructed limbs. The front-end status detection module uses a flexible packaging layer to package a printed circuit (Continued)

board, and after the surface of the flexible package layer is chemically treated, a pre-polymerized hydrogel solution is injected to carry out cross-linking to obtain a hydrogel adhesive layer, thereby ensuring long-time close attachment to the skin while avoiding bacterial infection on the surface of the skin. The back-end signal processing and outputting module processes blood oxygen saturation and temperature data, and transmits the data to a mobile terminal in real time. The present invention enables on-line monitoring of the blood flow health status of postoperative flaps and reconstructed limbs. When the blood oxygen saturation of the human body is below a normal value or when temperature and pulse signals are abnormal, the mobile terminal will trigger an alarm function, promptly alerting medical staff and the patient.

7 Claims, 2 Drawing Sheets

(51) Int. Cl.
| | | |
|---|---|---|
| *A61B 5/01* | (2006.01) | |
| *A61B 5/0205* | (2006.01) | |
| *A61B 5/024* | (2006.01) | |
| *A61B 5/1455* | (2006.01) | |

(52) U.S. Cl.
CPC ............ *A61B 5/6832* (2013.01); *A61B 5/725* (2013.01); *A61B 5/7475* (2013.01); *A61B 5/01* (2013.01); *A61B 5/02427* (2013.01); *A61B 5/14552* (2013.01); *A61B 2560/045* (2013.01); *A61B 2560/0462* (2013.01); *A61B 2562/0271* (2013.01); *A61B 2562/12* (2013.01); *A61B 2562/164* (2013.01); *A61B 2562/166* (2013.01)

(58) Field of Classification Search
CPC ..... A61B 5/7475; A61B 5/01; A61B 5/02427; A61B 5/14552; A61B 2560/045; A61B 2560/0462; A61B 2562/0271; A61B 2562/12; A61B 2562/164; A61B 2562/166

See application file for complete search history.

(56) References Cited

FOREIGN PATENT DOCUMENTS

| CN | 102675823 A | 9/2012 |
|---|---|---|
| CN | 109698071 A | 4/2019 |
| CN | 110236503 A | 9/2019 |
| CN | 110974249 A | 4/2020 |
| CN | 111234268 A | 6/2020 |
| CN | 113180618 A | 7/2021 |
| CN | 113336893 A | 9/2021 |
| EP | 0085327 A1 | 8/1983 |
| JP | 2011054345 A | 3/2011 |
| WO | 2017107658 A1 | 6/2017 |
| WO | 2017181129 A2 | 10/2017 |
| WO | 2019059753 A1 | 3/2019 |

OTHER PUBLICATIONS

Office Action issued in corresponding Chinese Application No. 202111074743.X, dated Sep. 23, 2022, 20 pages, with English translation.

Notice of Allowance issued in corresponding Chinese Application No. 202111074743.X, dated Mar. 1, 2023, with English translation.

ON-SKIN SENSING SYSTEM FOR DETECTING BLOOD FLOW STATUS IN POSTOPERATIVE FLAP AND RECONSTRUCTED LIMB

TECHNICAL FIELD

The present invention relates to the field of medical health monitoring, and more specifically, relates to an on-skin sensing system for detecting blood flow status in a postoperative flap and a reconstructed limb.

BACKGROUND ART

According to data provided by the American Cancer Society, in the past five years, there were about 252,710 new cases of breast cancer every year, and the total number of head and neck cancer patients has exceeded 822,000. Mastectomy is often employed for the treatment of breast cancer, and head and neck tumor ablation is often employed for the treatment of head and neck cancer. To improve the appearance of a patient's surgical site and to reduce the probability of wound infection, wound site reconstruction is especially important. Flap transplantation surgery greatly improves the reconstruction ability of skin tissue and effectively avoids infection in a postoperative site. The surgery can also reconstruct the features of sites such as the face, breasts, and limbs, and has been widely used in the rehabilitation treatment of the two kinds of cancer.

The specific process of flap transplantation surgery involves separating skin and blood vessels from one region of the body and reconnecting them to another region, and medical staff generally use microsurgery to reconnect the blood vessels. The success rate of flap transplantation surgery is 95% or higher, where flap failure is caused by vascular injury and ischemia of the transferred tissue, which mostly occur within 24 hours after surgery. The causes of vascular damage include pathological abnormalities in arteries and veins, such as extrinsic venous compression and venous thrombosis formation, and 17% of free flaps develop vascular injury during and after surgery. However, typically, clinical care and secondary surgical rescue have a reported rescue success rate of only 70% to 80%. In 1978, researchers confirmed that prolonged ischemia and lack of blood return resulted in significantly decreased success rates of surgical vascular reconstruction, swelling of ischemic vascular cells led to vessel collapse, and contraction of endothelial cells led to formation and proliferation of microthrombus. Flap ischemia for 12 hours will lead to failure of flap transplantation surgery. Therefore, early real-time flap status monitoring is very important for improving the success rate of flap transplantation and reducing vascular damage.

Routine monitoring of a postoperative flap is generally carried out by medical staff, who observe features of the flap such as color, degree of swelling, edema, temperature, and absence or presence of bleeding to determine the health status of the flap. However, these observation indexes lack a quantitative standard, and are highly reliant on the experience of the medical staff, thereby requiring training of the related medical staff. Since vascular injury to and ischemic symptoms in a flap may occur within 24 hours post surgery, the medical staff need to monitor the flaps of a patient on a regular basis, and thus need to repeatedly unwrap the bandage on the postoperative wound, which greatly troubles both the patient and the medical staff.

In recent years, researchers have successively developed a variety of novel flap detection techniques and instruments, including blood vessel detection techniques based on the blood flow in a flap; handheld Doppler ultrasonic apparatuses, implantable Doppler ultrasonic apparatuses, color ultrasonic apparatuses, fluorescent angiography, and laser Doppler blood flowmeters; techniques based on monitoring of tissue metabolism and ischemia: near infrared spectroscopy and microdialysis. These emerging testing instruments are of great significance for improving the success rate of flap transplantation and early warning of symptoms such as flap vascular injury and ischemia. However, the above measurement techniques still suffer from some limitations, such as implantation-based detection, non-continuous measurement, complex operation, high cost, large volume, among other defects. Hence, development of a low-cost, wearable, non-invasive on-skin sensing system for continuously detecting blood flow status in a postoperative flap and a reconstructed limb has broad application prospects.

According to flap failure cause analysis and novel flap detection techniques, it can be seen that the health status of the blood vessels of a postoperative flap is particularly important. Hence, the use of a non-invasive blood oxygen sensor to measure the blood oxygen of the flap can further quantify and determine the health status of the flap. The physical principle underlying the detection method is photoplethysmography, which detects changes in the amount of light absorption of the blood when a human blood vessel is pulsating, and performs calculation on the basis of the changes.

SUMMARY OF THE INVENTION

In view of the defects or the needs for improvement of the prior art described above, provided in the present invention is an on-skin sensing system for detecting blood flow status in a postoperative flap and a reconstructed limb. The invention aims to use structural design and employs a flexible material and a hydrogel adhesive layer to enable front-end blood oxygen and temperature signal detection modules to tightly attach to and conform to the skin of the human body, while ensuring long time detection and avoiding skin inflammations caused by bacterial growth. The invention also aims to by circuit design, enable a back-end signal processing module to receive, process and send sensing data of the front-end.

In order achieve the above aims, according to one aspect of the present invention, there is provided an on-skin sensing system for detecting blood flow status in a postoperative flap and a reconstructed limb, the system comprising a front-end status detection module and a back-end signal processing and outputting module, wherein the front-end status detection module uses a flexible packaging material as a packaging layer, and a surface of the packaging layer is provided with a hydrogel adhesive layer for attaching the front-end status detection module to a skin surface of a subject under test; the front-end status detection module is used to acquire a blood oxygen photoplethysmographic waveform and body temperature data of the subject under test;

the back-end signal processing and outputting module directly connects to the front-end status detection module and receives a blood oxygen photoplethysmographic waveform signal and the body temperature data, and the back-end signal processing and outputting module is used to perform processing and calculation on the blood oxygen photoplethysmographic waveform signal to obtain blood oxygen saturation and pulse signals of the subject under test, and then transmit the blood oxygen saturation, body temperature, and pulse signals of the subject under test to a mobile terminal.

Preferably, the front-end status detection module comprises a printed circuit board that uses a flexible material as a substrate, a blood oxygen detection circuit, and a body temperature detection circuit, and the blood oxygen detection circuit is used to acquire a blood oxygen photoplethysmographic waveform of the subject under test, and the body temperature detection circuit is used to detect body temperature data of the subject under test.

Preferably, the back-end signal processing and outputting module performs low-pass filtering and band-pass filtering, in a window of a fixed time domain length, on each of a red-light blood oxygen photoplethysmographic waveform and an infrared-light blood oxygen photoplethysmographic waveform acquired by the blood oxygen detection circuit, so as to obtain DC components and AC components of the blood oxygen photoplethysmographic waveforms, and then uses a peak searching algorithm to process the AC component of the infrared-light blood oxygen photoplethysmographic waveform to obtain peak positions of the photoplethysmographic waveform in the window, so as to calculate an average pulse within the fixed time domain length; and uses peak positions of the photoplethysmographic waveforms to determine the ratio of the AC component to the DC component of red light and that of infrared light at the peak points, and then maps the average ratios within the fixed time domain length to blood oxygen saturation by using a calibrated blood oxygen calculation formula, and moves the window according to equal-length time intervals, so as to obtain time series signals relating to blood oxygen saturation and pulses, and then transmits blood oxygen saturation and pulse signals to the mobile terminal in real time.

Preferably, the back-end signal processing and outputting module comprises a CC2640R2F core processing module, a power supply module, a Bluetooth radiofrequency module, a program burning module, and a clock crystal oscillator module; the program burning module is used to write programs and protocols that need to be run into the CC2640R2Fcore processing module; the power supply module is used to supply power to the CC2640R2F core processing module and the front-end status detection module; the Bluetooth radiofrequency module is used to communicatively connect to the mobile terminal; and the clock crystal oscillator module is used to assist in normal operation of the CC2640R2F core processing module.

Preferably, the hydrogel adhesive layer is prepared using precursor monomers, a solvent, and polymerization additives, wherein the precursor monomers comprise acrylamide in a mass fraction of 20-30 wt %, carboxymethyl chitosan in a mass fraction of 1-3 wt %, and tannic acid in a mass fraction of 0.5-2 wt %; the solvent comprises deionized water and glycerol in a volume ratio of 1:1; and the polymerization additives comprise N,N'-methylenebisacrylamide as a cross-linking agent and Irgacure 2959 as an initiator.

Preferably, the cross-linking agent N,N'-methylenebisacrylamide is in a mass fraction of 0.02-0.1 wt % of the acrylamide monomer, and the initiator Irgacure 2959 is in a mass fraction of 0.3-1 wt % of a prepolymerized hydrogel solution.

Preferably, the sensing system comprises preparation of the front-end status detection module and connection with the back-end signal processing and outputting module.

The preparation of the front-end status detection module comprises: fixing, onto a quartz glass plane, a printed circuit board designed to have a blood oxygen detection circuit and a body temperature detection circuit, and pouring a flexible packaging layer; bonding an acrylic plate mold onto the flexible packaging layer using a double-sided adhesive tape, and evenly coating a benzophenone/ethanol solution on the flexible packaging layer, wherein the mass ratio of benzophenone to ethanol in the benzophenone/ethanol solution is 2:48; performing benzophenone/ethanol solution treatment for 10 min, and after the solution treatment is completed, introducing nitrogen to blow the residual solution off the surface; injecting a pre-polymerized hydrogel solution onto the upper surface of the flexible packaging layer treated with the benzophenone/ethanol solution, and when the pre-polymerized hydrogel solution just overflows from the upper edge of the acrylic mold, stopping the injection; completely covering the acrylic plate mold with a quartz glass cover; placing the front-end status detection module covered with the quartz glass cover under a UV lamp having a power of 60 W and a wavelength of 365 nm, and illuminating the same for 40 min, so as to obtain a fully polymerized hydrogel adhesive layer; and finally, removing the quartz glass cover and the acrylic mold sequentially from the front-end status detection module, so as to obtain a front-end status detection module patch.

The connection with the back-end signal processing and outputting module comprises: selecting an MAX30102EFD+T blood oxygen detection chip and a TMP117AIDRVR semiconductor temperature sensor chip as the blood oxygen detection circuit and the body temperature detection circuit of the front-end status detection module, wherein each of the MAX30102EFD+T and the TMP117AIDRVR uses an I2C bus to communicate with the CC2640R2F core processing module of the back-end signal processing and outputting module, and can share the same SCL and SDA ports; selecting a CC2640R2FRHBR Bluetooth low-power consumption wireless MCU as the core processor of the back-end signal processing and outputting module, using DIO3 and DIO4 ports of the CC2640R2FRHBR as the SCL and SDA ports respectively for data communication with the front-end status detection module, and using the DIO10 port as an INT port to control the MAX30102EFD+T blood oxygen detection chip; selecting 24 MHz TSX-3225 and 32.768 kHz FC-135 passive crystal resonators from EPSON as the crystal oscillator of the external clock crystal oscillator circuit of the CC2640R2F core processing module; selecting AN2051-24 having an impedance of 50Ω as the Bluetooth antenna of the Bluetooth radiofrequency module; and selecting TPS63001DRCR as the booster chip of the power supply module, and a CR2032 button cell as the 3V input power supply of the power supply module.

Preferably, preparation of the pre-polymerized hydrogel solution comprises: sequentially adding an acrylamide monomer, an anti-bacterial monomer, and a viscous monomer solution to a glass sample bottle, and after sealing, sufficiently shaking the same uniformly on a shaker to obtain a precursor monomer mixture;

adding a mixed solution of deionized water and an organic alcohol to the obtained precursor monomer mixture, stirring to mix uniformly, adding a cross-linking agent and an initiator sequentially, and after sealing, placing the mixture in an ultrasonic machine to perform ultrasonic shaking, and upon complete dissolution of solutes in the glass sample bottle, performing degassing treatment to obtain the pre-polymerized hydrogel solution.

Preferably, the material of the flexible packaging layer can be a dark PDMS/carbon black mixed soft material, wherein the mass ratio of PDMS: carbon black is 100:1, and the mass ratio of a PDMS prepolymer to a curing agent is 10:1, the prepolymer and the curing agent are sequentially added to a plastic cup, and stirring is performed continuously for 5 minutes to ensure that the curing agent and the prepolymer are mixed uniformly; polydimethylsiloxane from which air bubbles have been removed is drawn at a uniform speed using a 1 ml medical syringe, and is uniformly coated on a wire substrate layer of the printed circuit board, the coating is left to stand for 2 min, and after the polydimethylsiloxane evenly spreads on the wire substrate layer of the printed circuit board, the printed circuit board is placed on a temperature-adjustable hot plate with the temperature adjusted to 90 degrees Celsius and is heated for 30 min, so as to prepare the flexible packaging layer on the wire substrate layer of the printed circuit board.

Overall, compared with the prior art, the above technical solutions conceived by means of the present invention facilitate large-scale mass production because of the use of printed circuit board processes. The front-end status detection module employs a printed circuit board that uses a flexible material as the substrate, and is covered on the surface with a hydrogel adhesive layer, thereby ensuring that the front-end status detection module can be attached to and remain conforming to the skin of a subject under test for a long time without causing skin infection, and offers excellent wearing comfort. The back-end signal processing and outputting module uses a low-power core processor which can perform ultra-long-time standby operation, and uses the Bluetooth 5.0 communication protocol such that the acquired data can be transmitted and analyzed quickly and stably. Although flap transplantation and limb reconstruction surgeries have achieved a success rate of 95% or higher in recent years, strict monitoring must be performed 24 hours after surgery. Routine monitoring of a postoperative flap is generally carried out by medical staff, who observe features of the flap such as color, swelling degree, edema, temperature, and absence or presence of bleeding to determine the health status of the flap. However, these observation indexes lack a highly quantitative standard, and are highly reliant on the experience of the medical staff. The present invention achieves quantitative display of the blood oxygen saturation, skin temperature and pulse of a flap or reconstructed limb. When a subject under test is in a critical condition, a mobile terminal human-computer interaction app will send out an alarm to inform medical staff, such that the patient can receive treatment in the shortest time possible. The present invention can not only increase the accuracy of clinical identification of the status of postoperative flaps and reconstructed limbs by medical staff, but also greatly reduce the work intensity of the medical staff, and thus has far-reaching significance.

BRIEF DESCRIPTION OF THE DRAWINGS

In all the drawings, the same reference sign is used to denote the same element or structure, wherein: 1—chip layer; 2—wire substrate layer of printed circuit board; 3—benzophenone/ethanol solution; 4—acrylic mold; 5—flexible packaging layer; 6—medical syringe; 7—prepolymerized hydrogel solution; 701—acrylamide; 702—N, N'-methylenebisacrylamide; 703—tannic acid; 704—glycerol; 705—Ir2959 photoinitiator; 706—carboxymethyl chitosan, 8—quartz glass cover; 9—UV lamp; 10—hydrogel adhesive layer; 11—front-end status detection module; 12—back-end signal processing and outputting module; 13—blood oxygen detection circuit; 14—body temperature detection circuit; 15—CC2640R2F core processing module; 16—power supply module; 17—Bluetooth radiofrequency module; 18—program burning module; 19—clock crystal oscillator module; 20—mobile terminal human-computer interaction app; 21—3 V button cell; 22—booster chip; and 23—decoupling capacitor.

DETAILED DESCRIPTION

In order for the purpose, technical solution, and advantages of the present invention to be clearer, the present invention is described in further detail below with reference to the accompanying drawings and embodiments. It should be appreciated that the specific embodiments described here are used merely to explain the present invention and are not used to limit the present invention. In addition, the technical features involved in various embodiments of the present invention described below can be combined with one another as long as they do not constitute a conflict therebetween.

Figure 2:
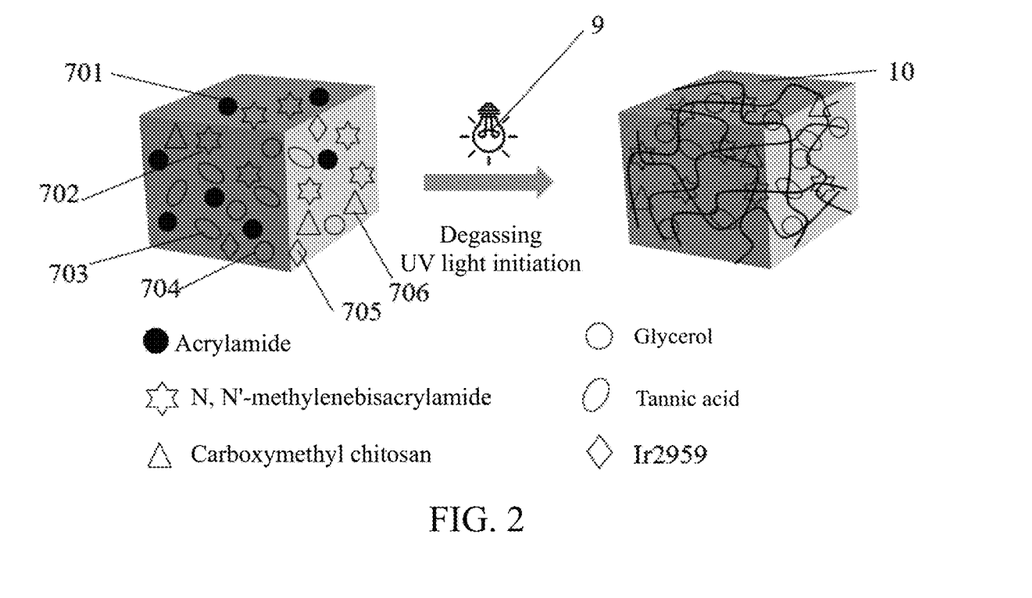
FIG. 2 is a schematic diagram showing the composition of a hydrogel adhesive layer of the on-skin sensing system for blood flow status in a postoperative flap and a reconstructed limb.
Figure 3:
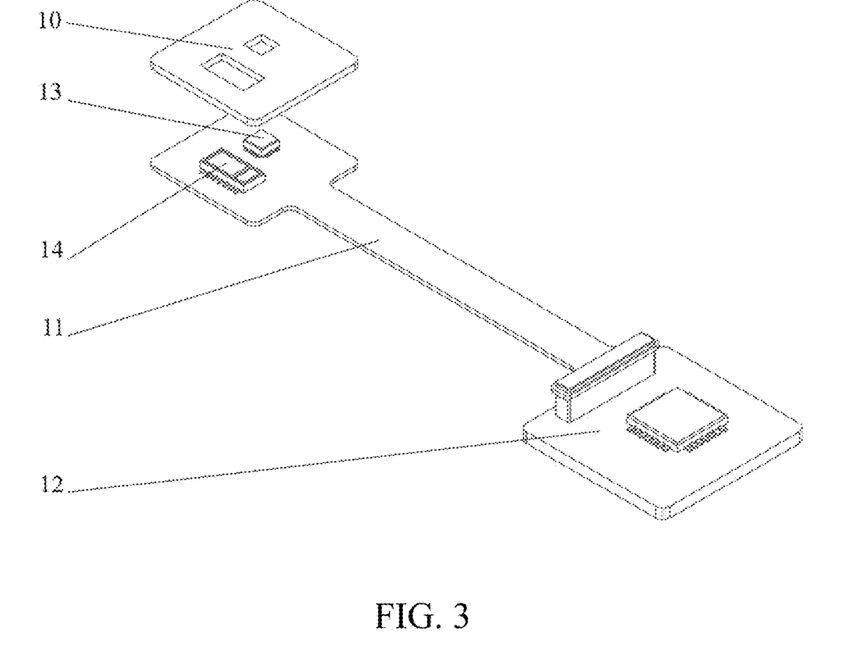
FIG. 3 is a schematic diagram showing the device structure of the on-skin sensing system for detecting blood flow status in a postoperative flap and a reconstructed limb.

As shown in FIG. 2, the present invention sets forth an on-skin sensing system for detecting blood flow status in a postoperative flap and a reconstructed limb. The system comprises a front-end status detection module 11, a back-end signal processing and outputting module 12, and a mobile terminal human-computer interaction app 20. The front-end status detection module 11 is a flexible printed circuit board (FPCB) using a flexible material as a substrate and integrating a blood oxygen detection circuit 13 and a body temperature detection circuit 14, and is configured to acquire a blood oxygen photoplethysmographic waveform and body temperature data of a subject under test. The surface of the printed circuit board is covered with a flexible packaging layer 5, and a hydrogel adhesive layer 10 is provided on the surface of the flexible packaging layer 5, such that the entire front-end status detection module 11 can be attached to the skin of the subject under test, while avoiding bacterial infection resulting from prolonged attachment.

For further illustration, the back-end signal processing and outputting module 12 performs low-pass filtering and band-pass filtering on each of an acquired red-light blood oxygen photoplethysmographic waveform and an acquired infrared-light blood oxygen photoplethysmographic waveform in a window of a fixed time domain length, so as to obtain DC components and AC components of the blood oxygen photoplethysmographic waveforms. A peak searching algorithm is used to process the AC component of the infrared-light blood oxygen photoplethysmographic waveform to obtain peak positions of the photoplethysmographic waveform in the window, so as to calculate an average pulse within the fixed time domain length. In addition to calculation of the average pulse, peak positions of the photoplethysmographic waveforms can also be used to determine the ratio of the AC component to the DC component of red light and that of infrared light at the peak points, and then the average ratios within the fixed time domain length can be mapped to blood oxygen saturation by using a calibrated blood oxygen calculation formula. The window is moved according to equal-length time intervals so as to obtain time series signals relating to blood oxygen saturation and pulses. The back-end signal processing and outputting module transmits the blood oxygen saturation, body temperature and pulse signals to the mobile terminal human-computer interaction app in real time by means of a Bluetooth radiofrequency module.

A mobile terminal platform corresponding to the mobile terminal human-computer interaction app is a smart phone or a personal computer. The mobile terminal human-computer interaction app can display, in real time, the blood oxygen saturation, body temperature and pulse signals of the subject under test. When the blood oxygen saturation and body temperature of the subject under test remain at a low level for a period of time, or the pulse signal of the subject under test is not detected, an alarm function inside the app will be activated. A user can control the operation and stopping of the entire detection system by means of the mobile terminal human-computer interaction app. The mobile terminal human-computer interaction app can store, locally on the mobile terminal platform, the received blood oxygen saturation, body temperature and pulses in real time according to time series.

For further illustration, the front-end status detection module 11 is directly connected to the back-end signal processing and outputting module 12 by means of a connection wire. The back-end signal processing and outputting module 12 provides stable working voltage and grounding potential for the front-end status detection module 11 through a connection wire, and the back-end signal processing and outputting module 12 can directly control the operation of the front-end status detection module 11. In turn, the front-end status detection module 11 directly transmits the acquired physiological signal data to the back-end signal processing and outputting module 12 through a connection wire.

For further illustration, the blood oxygen detection circuit 13 and the body temperature detection circuit 14 of the front-end status detection module 11 can use a commercially available blood oxygen detection chip and a commercially available semiconductor temperature sensor chip to realize the functions thereof. The blood oxygen detection chip integrates a photodiode, a red LED and an infrared LED. The blood oxygen detection chip and the semiconductor temperature sensing chip are not covered by the flexible packaging layer and the hydrogel adhesive layer 10, but are directly in contact with part of the skin of the subject under test so as to acquire the red-light blood oxygen photoplethysmographic waveform, the infrared-light blood oxygen photoplethysmographic waveform, and skin temperature data of the subject under test. The sampling rate of the blood oxygen detection circuit 13 is 100 Hz, and the sampling rate of the body temperature detection circuit 14 is 1 Hz.

For further illustration, the precursor monomers of the hydrogel adhesive layer 10 of the front-end status detection module 11 are respectively selected from acrylamide, carboxymethyl chitosan, and tannic acid, wherein the mass fractions are respectively 20-30 wt %, 1-3 wt %, and 0.5-2 wt %; the solvent of the hydrogel adhesive layer is deionized water and glycerol in a volume ratio of 1:1; the polymerization additives of the hydrogel adhesive layer include N,N'-methylenebisacrylamide as a cross-linking agent in a mass fraction of 0.02-0.1 wt % of the acrylamide monomer, and Irgacure 2959 as an initiator in a mass fraction of 0.3-1 wt % of a prepolymerized hydrogel solution.

As a preferred embodiment of the present invention, a method for preparing the hydrogel adhesive layer includes:
step 1: weighing 2.5 g of the acrylamide monomer, preparing the carboxymethyl chitosan monomer and the tannic acid monomer as uniform solutions, and uniformly dropping the solutions into a 30 ml glass bottle using a 1000-microliter pipette gun; shaking the mixture of the precursor monomers on a shaker until the solution is uniformly mixed;
step 2: injecting the deionized water and glycerol in a volume ratio of 1:1 into the 30 ml sample bottle at a uniform speed, and stirring the same with a glass rod for 30 min; sequentially adding, into the mixed solution, an aqueous solution of the cross-linking agent N,N'-methylenebisacrylamide, and the photoinitiator Irgacure 2959; performing ultrasonic shaking at the temperature of 25 degrees Celsius using an ultrasonic machine having a power of 100 W for 30 min; performing degassing by introducing nitrogen to the prepolymerized hydrogel solution at a uniform speed for 30 min to then obtain a completely degassed prepolymerized hydrogel solution; and
step 3: drawing the prepolymerized hydrogel solution at a uniform speed using a syringe, and injecting the prepolymerized hydrogel solution into an acrylic plate mold on the flexible packaging layer, wherein the flexible packaging layer needs to be soaked using a benzophenone/ethanol solution for 30 min; performing a sealing operation by means of covering the entire mold using a quartz glass sheet thereon; performing light-initiated polymerization for 40 min using an UV lamp having a power of 60 W and a wavelength of 365 nm, thereby obtaining the hydrogel adhesive layer.

Figure 4:
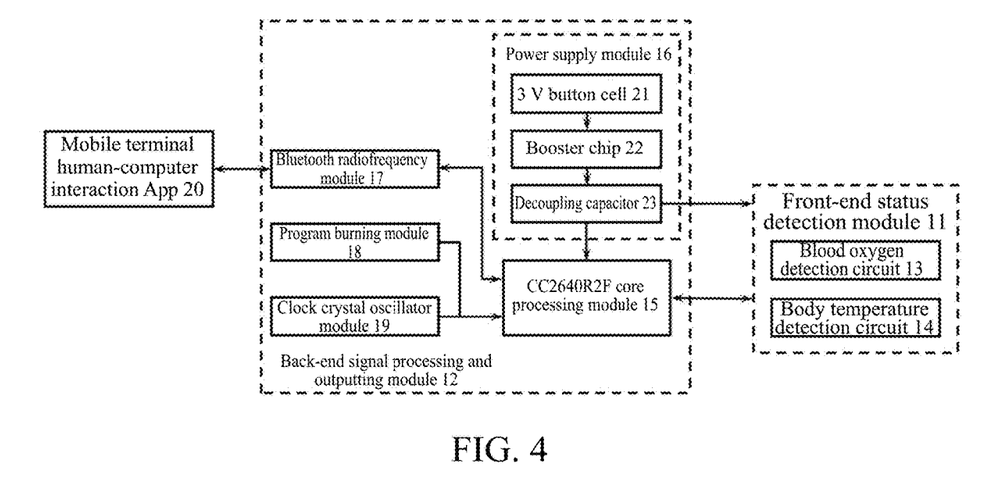
FIG. 4 is a diagram showing the principle of the circuit layout of the on-skin sensing system for detecting blood flow status in a postoperative flap and a reconstructed limb.

As a preferred embodiment of the present invention, considering the low power consumption and compactness of the entire system, the back-end signal processing and outputting module 12 can use the CC2640R2F series Bluetooth low-power wireless MCU from Texas Instruments as a core processor. The back-end signal processing and outputting module 12 is composed of a CC2640R2F core processing module 15, a program burning module 18, a clock crystal oscillator module 19, a Bluetooth radiofrequency module 17, and a power supply module 16. The CC2640R2F core processing module 15 can control the operation of the front-end status detection module 11, analyze and process physiological signals acquired by the front-end status detection module 11, and perform data communication with the mobile terminal human-computer interaction app 20 through the Bluetooth radiofrequency module 17. The program burning module 18 is used to write programs and protocols that need to be run for the back-end signal processing and outputting module 12 into the CC2640R2F core processing module 15. The clock crystal oscillator module 19 is used to assist in the normal operation of the CC2640R2F core processing module 15, and the clock crystal oscillator module 19 uses two passive crystal resonators respectively of 24 MHZ and 32.768 kHz. The Bluetooth radiofrequency module 17 uses differential antennas to ensure excellent data communication, and the impedance of the Bluetooth radiofrequency antenna is 50Ω. The power supply module 16 is composed of a button cell 21 having an output voltage of 3 V, a booster chip 22, and a decoupling capacitor 23. The voltage of the button cell is processed by the booster chip 22 such that a stable voltage of 3.3 V is outputted, and then decoupling is performed by means of two 100 nF grounding capacitors connected in parallel to supply power to the hardware layer of the entire system.

As a preferred embodiment of the present invention, the back-end signal processing and outputting module 12 converts, by means of a particular blood oxygen algorithm, the red-light blood oxygen photoplethysmographic waveform and the infrared-light blood oxygen photoplethysmographic waveform acquired by the front-end status detection module 11 into blood oxygen saturation and pulse signals, and outputs the signals. The process of the particular blood oxygen algorithm is as follows:

In step 1, the sampling rate of the blood oxygen detection circuit of the front-end status detection module is 100 Hz, and windows having a time domain length of 5 s are set. When the back-end signal processing and outputting module controls the front-end status detection module to start running, data of a received red-light blood oxygen photoplethysmographic waveform data and data of a received infrared-light blood oxygen photoplethysmographic waveform are passed into respective windows. When the length of the data reaches the length of the windows, first, low-pass filtering is performed once at 0.5 Hz on the data of the red-light blood oxygen photoplethysmographic waveform and the data of the infrared-light blood oxygen photoplethysmographic waveform in the windows respectively, so as to obtain DC components of the red-light blood oxygen photoplethysmographic waveform and the infrared-light blood oxygen photoplethysmographic waveform respectively; then band-pass filtering is performed once at 0.5 Hz to 5 Hz on the data of the red-light blood oxygen photoplethysmographic waveform and the data of the infrared-light blood oxygen photoplethysmographic waveform in the windows respectively, so as to obtain AC components of the red-light blood oxygen photoplethysmographic waveform and the infrared-light blood oxygen photoplethysmographic waveform respectively.

In step 2, a particular peak searching algorithm is used to process the AC component of the infrared-light blood oxygen photoplethysmographic waveform, so as to obtain peak positions of the infrared-light blood oxygen photoplethysmographic waveform in the window, which are also the peak positions of the red-light blood oxygen photoplethysmographic waveform in the window. The blood oxygen volume waveform is equivalent to the pulse waveform of the human body to a certain extent, so the average pulse of the subject under test within 5 s can be calculated by means of the peak positions of the blood oxygen photoplethysmographic waveform in the window.

In step 3, the average ratio D1 of the DC component to the AC component of red light at corresponding peak positions and the average ratio D2 of the DC component to the AC component of infrared light at corresponding peak positions can be determined according to the peak positions of the blood oxygen photoplethysmographic waveforms in the windows. Then, the average ratios are mapped to blood oxygen saturation data using the blood oxygen calculation formula $$S_{pO_2} = A \cdot \left(\frac{D_1}{D_2}\right)^2 + B \cdot \frac{D_1}{D_2} + C$$

calibrated according to the Lambert-Beer law, where A, B, and C are constants obtained from a large number of experimental data.

In step 4, the average pulse and blood oxygen saturation signals obtained by calculation are transmitted to the mobile terminal human-computer interaction app by means of the Bluetooth radiofrequency module. When the length of the data of the blood oxygen photoplethysmographic waveforms received again by the back-end signal processing and outputting module reaches 1 s, the window having a time domain length of 5 s will be moved backward by a data length of 1 s, and the above step is repeated to calculate the average pulse and blood oxygen saturation signals, which are then transmitted to the mobile terminal human-computer interaction app.

As a preferred embodiment of the present invention, the front-end status detection module 11 employs a printed circuit board that uses a flexible material as a substrate, so as to ensure the portability and comfort of the device, such that the device can conform well to the skin of the subject under test. The back-end signal processing and outputting module 12 can employ a conventional printed circuit board process, or can employ a printed circuit board process that uses a flexible material as a substrate, as is the case with the front-end status detection module.

The technical solutions of the present invention will be further illustrated below by way of specific embodiments.

The present invention provides an on-skin sensing system for detecting blood flow status in a postoperative flap and a reconstructed limb. The system can acquire blood oxygen saturation, skin temperature and pulse signals of a subject under test, and communicate with a mobile terminal human-computer interaction app by means of Bluetooth.

Figure 1:
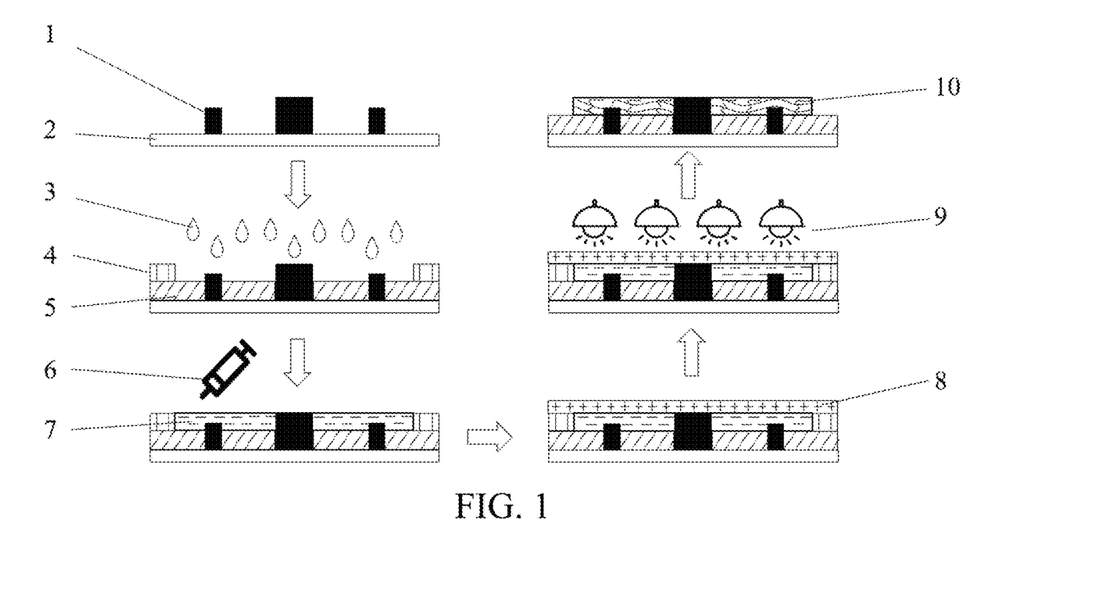
FIG. 1 is a schematic diagram showing a preparation process of a front-end status detection module of the on-skin sensing system for detecting blood flow status in a postoperative flap and a reconstructed limb.

FIG. 1 is a schematic diagram showing a preparation method of the front-end status detection module of the on-skin sensing system for detecting blood flow status in a postoperative flap and a reconstructed limb. The preparation process of the front-end status detection module is described below in conjunction with examples.

An MAX30102EFD+T blood oxygen detection chip and a TMP117AIDRVR semiconductor temperature sensor chip were selected to realize the functions of the blood oxygen detection circuit 13 and the body temperature detection circuit 14 of the front-end status detection module 11. Each of the MAX30102EFD+T and the TMP117AIDRVR used an I2C bus to communicate with the CC2640R2F core processing module 15 of the back-end signal processing and outputting module 12, and could share the same SCL and SDA ports.

A CC2640R2FRHBR Bluetooth low-power consumption wireless MCU was selected as the core processor of the back-end signal processing and outputting module 12. The DIO3 and DIO4 ports of the CC2640R2FRHBR were used as the SCL and SDA ports respectively for data communication with the front-end status detection module, and the DIO10 port was used as an INT port to control the MAX30102EFD+T blood oxygen detection chip. 24 MHz TSX-3225 and 32.768 kHz FC-135 passive crystal resonators from EPSON were selected as the crystal oscillator of the external clock crystal oscillator module 19 of the CC2640R2F core processing module 15. AN2051-24 having an impedance of 50Ω was selected as the Bluetooth antenna of the Bluetooth radiofrequency module 17, and the circuit employed a differential design to enhance signal stability. TPS63001DRCR was selected as the booster chip of the power supply module 16, and a CR2032 button cell was selected as the 3V input power supply of the power supply module 16.

A printed circuit board designed to have a blood oxygen detection circuit and a body temperature detection circuit was fixed onto a quartz glass plane, and the entire printed circuit board was ensured to be level. Before pouring a flexible packaging layer 5, a wire substrate layer 2 of the printed circuit board and a chip layer 1 were wiped with a dry paper towel to remove dust from the surfaces thereof to ensure that the surfaces were free of impurities.

The material of the flexible packaging layer could be a dark PDMS/carbon black mixed soft material, wherein the mass ratio of PDMS to carbon black was 100:1, and wherein the mass ratio of a PDMS prepolymer to a curing agent was 10:1. The prepolymer and the curing agent were sequentially added to a plastic cup, and stirring was performed continuously for 5 minutes to ensure that the curing agent and the prepolymer were mixed uniformly. In order to remove air bubbles therein, the stirred and mixed prepolymer was placed in a vacuum drying chamber to undergo vacuuming, and was left to stand for half an hour. After air bubbles were completely eliminated, the prepolymer was removed. The air pressure of the vacuum chamber was 0-0.1 atm. Then, the polydimethylsiloxane from which air bubbles have been removed was drawn at a uniform speed using a 1 ml medical syringe, and was uniformly coated on the wire substrate layer 2 of the printed circuit board. The coating was left to stand for 2 min. After the polydimethylsiloxane evenly spread on the wire substrate layer 2 of the printed circuit board, the device was placed on a temperature-adjustable hot plate with the temperature adjusted to 90 degrees Celsius, and the device was heated for 30 min, so as to prepare the flexible packaging layer 5 on the wire substrate layer 2 of the printed circuit board.

Next, an acrylic plate mold 4 was bonded onto the flexible packaging layer 5 using a double-sided adhesive tape, and a benzophenone/ethanol solution 3 was evenly coated on the flexible packaging layer, wherein the mass ratio of benzophenone to ethanol in the benzophenone/ethanol solution 3 was 2:48, and the treatment using the benzophenone/ethanol solution 3 was performed for 10 min; after the solution treatment was completed, nitrogen was introduced to blow the residual solution off the surface.

Then, a medical syringe 6 was used to inject a pre-polymerized hydrogel solution 7 onto the upper surface of the flexible packaging layer 5 treated with the benzophenone/ethanol solution 3. When the pre-polymerized hydrogel solution 7 just overflowed from the upper edge of the acrylic mold 4, injection was stopped.

Next, the acrylic plate mold 4 was completely covered with a quartz glass cover 8. Air bubbles should be prevented from occurring in the prepolymerized hydrogel solution 7 during this operation.

Subsequently, the front-end status detection module 11 covered with the quartz glass cover 8 was placed under a UV lamp 9 having a power of 60 W and a wavelength of 365 nm, and was illuminated for 40 min, so as to obtain a fully polymerized hydrogel adhesive layer 10.

Finally, the quartz glass cover 8 and the acrylic mold 4 were sequentially removed from the front-end status detection module, so as to obtain a front-end status detection patch.

Regarding this example, a schematic diagram showing the composition of the hydrogel adhesive layer of the on-skin sensing system for detecting blood flow status in a postoperative flap and a reconstructed limb is as shown in FIG. 2.

As shown in FIG. 2, the pre-polymerized hydrogel solution 7 included acrylamide monomer 701, N,N'-methylenebisacrylamide 702, tannic acid 703, glycerol 704, Ir2959 photoinitiator 705, and carboxymethyl chitosan 706. The mass fractions of the acrylamide 701, carboxymethyl chitosan 706, and tannic acid 703 were 20-30 wt %, 1-3 wt %, and 0.5-2 wt %, respectively. Further preferably, the acrylamide monomer 701 was weighed at a mass of 2.5 g. The carboxymethyl chitosan 706 and the tannic acid 703 were prepared as an aqueous carboxymethyl chitosan solution and a tannic acid solution respectively, and the solutions were drawn by a 1000-microliter pipette gun and were uniformly dropped into a 30 ml glass bottle. The precursor monomer mixture was shaken on a shaker until the solution was uniformly mixed. Deionized water and glycerol were provided in a volume ratio of 1:1, and were injected into the 30 ml sample bottle at a uniform speed. Stirring was performed using a glass rod for 30 min. An aqueous solution of the N,N'-methylenebisacrylamide 702 as the cross-linking agent and Irgacure 2959 as the initiator were added to the mixed solution sequentially. Ultrasonic shaking was performed at the temperature of 25 degrees Celsius using an ultrasonic machine having a power of 100 W for 30 min. Degassing was performed by introducing nitrogen to the prepolymerized hydrogel solution 7 at a uniform speed for 30 min to then obtain a completely degassed prepolymerized hydrogel solution 7. At the same time, the pre-polymerized hydrogel solution 7 was injected into the mold 4 on the flexible packaging layer 5, wherein the flexible packaging layer 5 needed to be soaked using the benzophenone/ethanol solution 3 for 30 min. The acrylic mold 4 was completely covered using the quartz glass cover 8 thereon. UV light-initiated polymerization was carried out for 40 min, thereby obtaining the hydrogel adhesive layer 10.

Regarding this example, a schematic diagram showing the principle of the circuit of the on-skin sensing system for detecting blood flow status in a postoperative flap and a reconstructed limb is shown in FIG. 4. Firstly, programs and protocols that need to be run were written into the CC2640R2F core processing module 15 by means of the program burning module 18 of the back-end signal processing and outputting module, and then a user used the mobile terminal human-computer interaction app 20 to control, by Bluetooth, the underlying hardware system to start running. The blood oxygen detection circuit 13 and the body temperature detection circuit 14 of the front-end status detection module 11 transmitted acquired data of the red-light and infrared-light blood oxygen photoplethysmographic waveforms and acquired body temperature data to the CC2640R2F core processing module 15 of the back-end signal processing and outputting module 12 through the I2C bus to perform processing and analysis. Then, the CC2640R2F core processing module 15 transmitted the blood oxygen saturation, body temperature and pulse signals obtained after processing to the mobile terminal human-computer interaction app 20 by means of the Bluetooth radiofrequency module 17 for real-time displaying.

The on-skin sensing system for detecting blood flow status in a postoperative flap and a reconstructed limb of the present invention needs to be used in conjunction with a specially designed mobile terminal human-computer interaction app. Wireless Bluetooth communication with the mobile terminal human-computer interaction app 20 is achieved by means of the Bluetooth radiofrequency module 17 of the back-end signal processing and outputting module to transmit blood oxygen saturation, body temperature and pulse data. The app is simple and convenient to operate without requiring much professional knowledge, and has a friendly human-computer interaction interface, and can adapt to people of different ages.

It can be easily understood by a person skilled in the art that the foregoing description is only preferred embodiments of the present invention and is not intended to limit the present invention. Any modifications, identical replacements, improvements and so on that are within the spirit and principle of the present invention should be included in the scope of protection of the present invention.

The invention claimed is:

1. An on-skin sensing system for detecting blood flow status in a postoperative flap and a reconstructed limb, comprising: a front-end status detection module and a back-end signal processing and outputting module, wherein
the front-end status detection module uses a flexible packaging material as a packaging layer, and a surface of the packaging layer is provided with a hydrogel adhesive layer for attaching the front-end status detection module to a skin surface of a subject under test; the front-end status detection module is used to acquire a blood oxygen photoplethysmographic waveform and body temperature data of the subject under test;
the back-end signal processing and outputting module directly connects to the front-end status detection module and receives a blood oxygen photoplethysmographic waveform signal and body temperature data, and the back-end signal processing and outputting module is used to perform processing and calculation on the blood oxygen photoplethysmographic waveform signal to obtain blood oxygen saturation and pulse signals of the subject under test, and then transmit the blood oxygen saturation, body temperature, and pulse signals of the subject under test to a mobile terminal;
wherein the hydrogel adhesive layer is prepared using precursor monomers, a solvent, and polymerization additives, wherein the precursor monomers comprise acrylamide in a mass fraction of 20-30 wt %, carboxymethyl chitosan in a mass fraction of 1-3 wt %, and tannic acid in a mass fraction of 0.5-2 wt %; the solvent comprises deionized water and glycerol in a volume ratio of 1:1; and the polymerization additives comprise N,N'-methylenebisacrylamide as a cross-linking agent and Irgacure 2959 as an initiator;
wherein the cross-linking agent N,N'-methylenebisacrylamide is in a mass fraction of 0.02-0.1 wt % of the acrylamide monomer; and the initiator Irgacure 2959 is in a mass fraction of 0.3-1 wt % of a prepolymerized hydrogel solution;
a connection with the back-end signal processing and outputting module comprises: selecting an MAX30102EFD+T blood oxygen detection chip and a TMP117AIDRVR semiconductor temperature sensor chip as the blood oxygen detection circuit and the body temperature detection circuit of the front-end status detection module, wherein each of the MAX30102EFD+T and the TMP117AIDRVR uses an I2C bus to communicate with a CC2640R2F core processing module of the back-end signal processing and outputting module, and shares the same SCL and SDA ports; selecting a CC2640R2FRHBR Bluetooth low-power consumption wireless MCU as the core processor of the back-end signal processing and outputting module, using DIO3 and DIO4 ports of the CC2640R2FRHBR as the SCL and SDA ports respectively for data communication with the front-end status detection module, and using the DIO10 port as an INT port to control the MAX30102EFD+T blood oxygen detection chip; selecting 24 MHz TSX-3225 and 32.768 kHz FC-135 passive crystal resonators from EPSON as the crystal oscillator of the external clock crystal oscillator circuit of the CC2640R2F core processing module; selecting AN2051-24 having an impedance of 50Ω as the Bluetooth antenna of the Bluetooth radiofrequency module; and selecting TPS63001DRCR as a booster chip of the power supply module, and a CR2032 button cell as the 3V input power supply of the power supply module;

wherein a method for preparing the hydrogel adhesive layer includes:

step 1: weighing 2.5 g of the acrylamide monomer, preparing the carboxymethyl chitosan monomer and the tannic acid monomer as uniform solutions, and uniformly dropping the solutions into a 30 ml glass bottle using a 1000-microliter pipette gun; shaking the mixture of the precursor monomers on a shaker until the solution is uniformly mixed;

step 2: injecting the deionized water and glycerol in a volume ratio of 1:1 into the 30 ml sample bottle at a uniform speed, and stirring the same with a glass rod for 30 min; sequentially adding, into the mixed solution, an aqueous solution of the cross-linking agent N,N'-methylenebisacrylamide, and the photoinitiator Irgacure 2959; performing ultrasonic shaking at the temperature of 25 degrees Celsius using an ultrasonic machine having a power of 100 W for 30 min; performing degassing by introducing nitrogen to the pre-polymerized hydrogel solution at a uniform speed for 30 min to then obtain a completely degassed prepolymerized hydrogel solution; and step 3: drawing the prepolymerized hydrogel solution at a uniform speed using a syringe, and injecting the prepolymerized hydrogel solution into an acrylic plate mold on the flexible packaging layer, wherein the flexible packaging layer needs to be soaked using a benzophenone/ethanol solution for 30 min; performing a sealing operation by means of covering the entire mold using a quartz glass sheet thereon; performing light-initiated polymerization for 40 min using an UV lamp having a power of 60 W and a wavelength of 365 nm, thereby obtaining the hydrogel adhesive layer.

2. The on-skin sensing system for detecting blood flow status in a postoperative flap and a reconstructed limb according to claim 1, wherein the front-end status detection module comprises a printed circuit board that uses a flexible material as a substrate, a blood oxygen detection circuit, and a body temperature detection circuit; the blood oxygen detection circuit and the body temperature detection circuit are disposed on the printed circuit board, the blood oxygen detection circuit is used to acquire a blood oxygen photoplethysmographic waveform of the subject under test, and the body temperature detection circuit is used to detect body temperature data of the subject under test.

3. The on-skin sensing system for detecting blood flow status in a postoperative flap and a reconstructed limb according to claim 2, wherein the back-end signal processing and outputting module performs low-pass filtering and band-pass filtering, in a window of a fixed time domain length, on each of a red-light blood oxygen photoplethysmographic waveform and an infrared-light blood oxygen photoplethysmographic waveform acquired by the blood oxygen detection circuit, so as to obtain DC components and AC components of the blood oxygen photoplethysmographic waveforms, and then uses a peak searching algorithm to process the AC component of the infrared-light blood oxygen photoplethysmographic waveform to obtain peak positions of the photoplethysmographic waveform in the window, so as to calculate an average pulse within the fixed time domain length; and uses peak positions of the photoplethysmographic waveforms to determine the ratio of the AC component to the DC component of red light and that of infrared light at the peak points, and then maps the average ratios within the fixed time domain length to blood oxygen saturation by using a calibrated blood oxygen calculation formula, and moves the window according to equal-length time intervals, so as to obtain time series signals relating to blood oxygen saturation and pulses, and then transmits blood oxygen saturation and pulse signals of the subject under test to the mobile terminal in real time.

4. The on-skin sensing system for detecting blood flow status in a postoperative flap and a reconstructed limb according to claim 3, characterized in that wherein the back-end signal processing and outputting module comprises a CC2640R2F core processing module, a power supply module, a Bluetooth radiofrequency module, a program burning module, and a clock crystal oscillator module; the program burning module is used to write programs and protocols that need to be run into the CC2640R2F core processing module; the power supply module is used to supply power to the CC2640R2F core processing module and the front-end status detection module; the Bluetooth radiofrequency module is used to communicatively connect to the mobile terminal; and the clock crystal oscillator module is used to assist in normal operation of the CC2640R2F core processing module.

5. The on-skin sensing system for detecting blood flow status in a postoperative flap and a reconstructed limb according to claim 1, wherein preparation of the front-end status detection module comprises: fixing, onto a quartz glass plane, a printed circuit board designed to have a blood oxygen detection circuit and a body temperature detection circuit, and pouring a flexible packaging layer; bonding an acrylic plate mold onto the flexible packaging layer using a double-sided adhesive tape, and evenly coating a benzophenone/ethanol solution on the flexible packaging layer, wherein the mass ratio of benzophenone to ethanol in the benzophenone/ethanol solution is 2:48; performing benzophenone/ethanol solution treatment for 10 min, and after the solution treatment is completed, introducing nitrogen to blow the residual solution off the surface; injecting a pre-polymerized hydrogel solution onto the upper surface of the flexible packaging layer treated with the benzophenone/ethanol solution, and when the pre-polymerized hydrogel solution just overflows from the upper edge of the acrylic mold, stopping injection; completely covering the acrylic plate mold with a quartz glass cover; placing the front-end status detection module covered with the quartz glass cover under a UV lamp having a power of 60 W and a wavelength of 365 nm, and illuminating the same for 40 min, so as to obtain a fully polymerized hydrogel adhesive layer; and finally, removing the quartz glass cover and the acrylic mold sequentially from the front-end status detection module, so as to obtain a front-end status detection module patch.

6. The on-skin sensing system for detecting blood flow status in a postoperative flap and a reconstructed limb according to claim 5, wherein preparation of the pre-polymerized hydrogel solution comprises: sequentially adding an acrylamide monomer, an anti-bacterial monomer, and a viscous monomer solution to a glass sample bottle, and after sealing, sufficiently shaking the same uniformly on a shaker to obtain a precursor monomer mixture;

adding a mixed solution of deionized water and an organic alcohol to the obtained precursor monomer mixture, stirring to mix uniformly, adding a cross-linking agent and an initiator sequentially, and after sealing, placing the mixture in an ultrasonic machine to perform ultrasonic shaking, and upon complete dissolution of solutes in the glass sample bottle, performing degassing treatment to obtain the pre-polymerized hydrogel solution.

7. The on-skin sensing system for detecting blood flow status in a postoperative flap and a reconstructed limb according to claim 5, wherein the material of the flexible packaging layer is a dark PDMS/carbon black mixed soft material, wherein the mass ratio of PDMS: carbon black is 100:1, and the mass ratio of a PDMS prepolymer to a curing agent is 10:1, the prepolymer and the curing agent are sequentially added to a plastic cup, and stirring is performed continuously for 5 minutes to ensure that the curing agent and the prepolymer are mixed uniformly; polydimethylsiloxane from which air bubbles have been removed is drawn at a uniform speed using a 1 ml medical syringe, and is uniformly coated on a wire substrate layer of the printed circuit board, the coating is left to stand for 2 min, and after the polydimethylsiloxane evenly spreads on the wire substrate layer of the printed circuit board, the printed circuit board is placed on a temperature-adjustable hot plate with the temperature adjusted to 90 degrees Celsius and is heated for 30 min, so as to prepare the flexible packaging layer on the wire substrate layer of the printed circuit board.

\* \* \* \* \*